United States Patent [19]

Corso, Jr. et al.

[11] Patent Number: 5,281,200
[45] Date of Patent: Jan. 25, 1994

[54] MULTIPLE COMPONENT BALLOON CATHETER SYSTEM AND STENOSIS TREATMENT PROCEDURE

[75] Inventors: Philip P. Corso, Jr.; Willard W. Hennemann, III, both of Davie, Fla.

[73] Assignee: Cordis Corporation, Miami Lakes, Fla.

[21] Appl. No.: 986,982

[22] Filed: Dec. 8, 1992

[51] Int. Cl.$^5$ .............................. A61M 29/00
[52] U.S. Cl. ........................ 604/96; 606/194
[58] Field of Search ..................... 604/96–101; 606/194, 195, 192

[56] References Cited

U.S. PATENT DOCUMENTS

| | | | |
|---|---|---|---|
| 4,195,637 | 4/1980 | Gruntzig et al. | 128/348 |
| 4,198,981 | 4/1980 | Sinnreich | 128/344 |
| 4,295,464 | 10/1981 | Shihata | 128/1 R |
| 4,327,720 | 5/1982 | Bronson et al. | 128/207.15 |
| 4,338,942 | 7/1982 | Fogarty | 128/344 |
| 4,714,460 | 12/1987 | Calderon | 604/28 |
| 4,846,174 | 7/1989 | Willard et al. | 128/344 |
| 4,911,163 | 3/1990 | Fina | 606/192 |
| 5,102,390 | 4/1992 | Crittenden et al. | 604/96 |
| 5,180,367 | 1/1993 | Kontos et al. | 604/101 |

*Primary Examiner*—Jerome L. Kruter
*Attorney, Agent, or Firm*—Lockwood, Alex, Fitzgibbon & Cummings

[57] ABSTRACT

A balloon catheter system is provided which includes a balloon-on-a-wire assembly and an over-the-wire catheter which slidably passes over the elongated body of the balloon-on-a-wire assembly, but not over its balloon. In the procedure by which the system is used, the balloon-on-a-wire assembly achieves an initial dilation or predilation of a lesion or stenosis, after which it is moved somewhat distally to clear the predilated stenosis. The over-the-wire catheter then is slidably moved over the balloon-on-a-wire assembly until its balloon reaches and dilates the predilated stenosis. After dilation is completed, the system is removed from the body vessel thus treated.

10 Claims, 2 Drawing Sheets

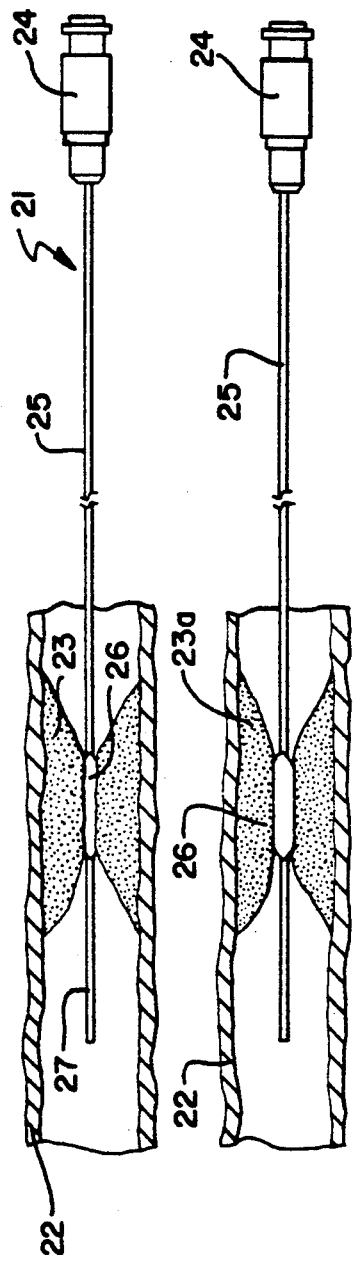
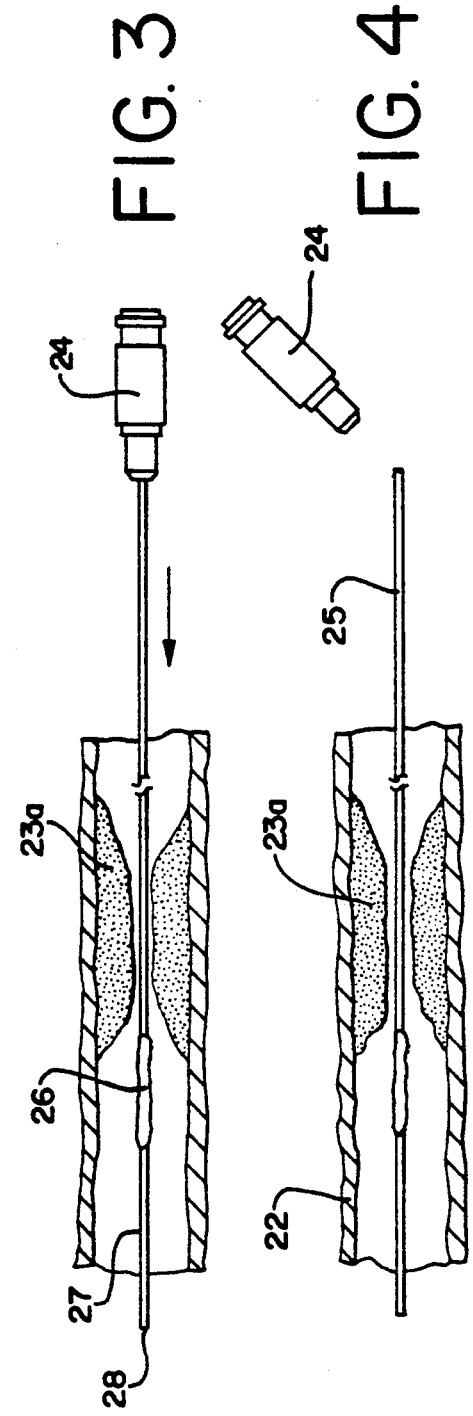
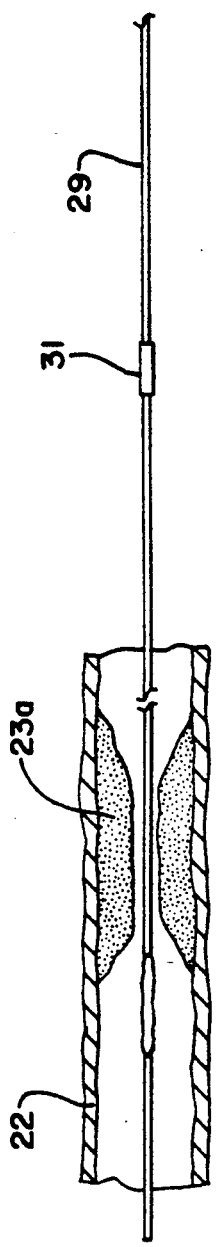

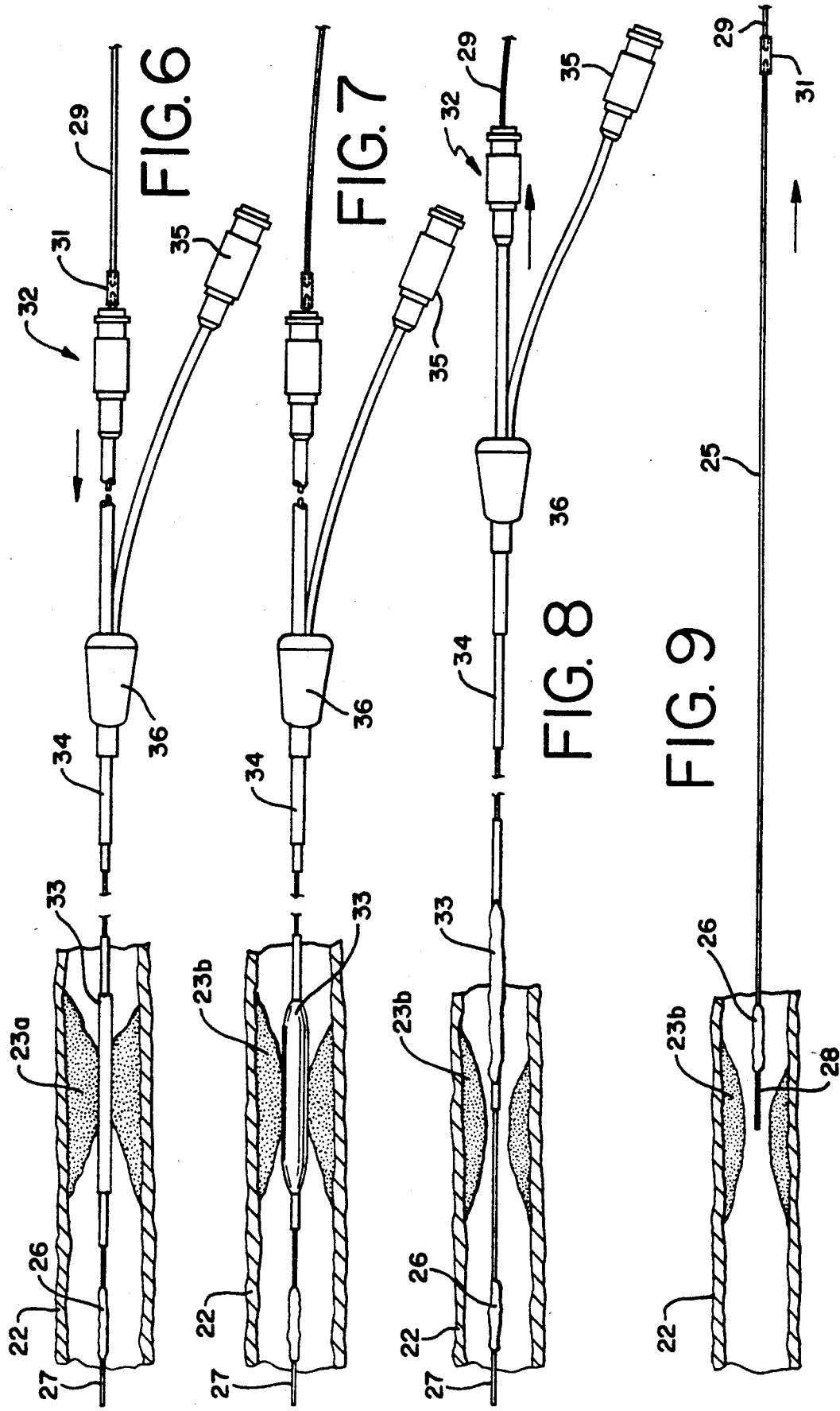

MULTIPLE COMPONENT BALLOON CATHETER SYSTEM AND STENOSIS TREATMENT PROCEDURE

BACKGROUND OF THE INVENTION

The present invention generally relates to procedures and devices for angioplasty treatments and the like. More specifically, the invention relates to improvements in catheter systems and angioplasty procedures for treating stenoses in blood vessels and other vessels of living bodies.

Balloon angioplasty procedures have been shown to be efficient and effective treatments to open arteries and other body passages occluded with plaque. These procedures generally involve insertion of a balloon catheter into the occlusion, or stenosis. The balloon, which is located at or near the distal end of the catheter, is then inflated, compressing the plaque to the arterial wall and dilating the stenosis or lesion within the artery, for example.

Often balloon catheters cannot be easily negotiated through branching vessels such as arterial branches and to the location of the stenosis. To help maneuver the catheters into place, physicians first insert a more maneuverable guidewire through the vessel and branches to the stenosis location. Then the balloon catheter is slidably inserted over the guidewire to and through the stenosis. After balloon inflation, the catheter and guidewire are removed. A limitation of this approach is that the stenoses must be open enough to permit insertion of the balloon catheter therethrough. Patients who suffer from tight stenoses typically are obliged to undergo the risk and expense of heart bypass surgery.

Prior approaches to address the difficulties of especially narrow stenoses include the use of microdilation probes, dilating guidewires, and similar devices. These approaches have permitted angioplasty treatment to many patients who otherwise would have undergone heart bypass surgery. Approaches such as those of U.S. Pat. Nos. 4,846,174 and 5,102,390 call for insertion of a guidewire, then insertion of the balloon catheter to the stenosis. If the stenosis is too occluded to permit insertion of the uninflated balloon catheter, approaches such as these call for removal of the guidewire while holding the balloon catheter on the proximal side of the stenosis. The physician then inserts a microdilation probe, dilating guidewire, or similar device though the balloon catheter and to and through the stenosis. The microdilation probe and dilating guidewire can consist of a "spring tip" guidewire with a balloon on the proximal side of the tip. The balloon of the microdilation probe, dilating guidewire, or similar device is then inflated, creating an opening sufficiently large to permit insertion of the balloon catheter. The deflated microdilation probe, dilating guidewire, or similar device could be located proximally, distally, or still within the stenosis. Inflation of the balloon catheter further dilates the stenosis.

The present invention improves upon approaches such as these while accomplishing the following objects.

It is a general object of this invention to provide an improved combination catheter device and method of its use, while reducing the steps required to perform an angioplasty procedure.

Another object of this invention is to provide an improved device and procedure which avoid having a guidewire type of member pass distally of a lesion more than once during the entire procedure.

Another object of the present invention is to improve angioplasty devices and procedures so that angioplasty procedures are available to patients who might otherwise require heart bypass surgery.

Another object of this invention is to reduce risk to the patient due to potential disassembly of components while in the body.

SUMMARY OF THE INVENTION

The present invention generally includes the combination of a fixed wire percutaneous transluminal angioplasty (PTCA) balloon dilatation catheter and a guidewire compatible over-the-wire PTCA balloon catheter for use in coronary and vascular angioplasty procedures. Hereinafter, the fixed wire PTCA balloon dilatation catheter shall be designated as a balloon-on-a-wire assembly, and the guidewire compatible over-the-wire PTCA balloon catheter shall be designated as a balloon catheter assembly.

The balloon-on-a-wire assembly has a balloon positioned at or near the distal end portion of a wire. The balloon-on-a-wire is intended to be inserted through the patient's arterial system or the like and to the stenosis in substantially the same manner as is a standard guidewire. The profile of the wire is generally the same as a standard guidewire, permitting comparable maneuverability in order to access the stenosis. The balloon-on-a-wire assembly is then inserted into the stenosis and inflated to predilate the stenosis, deflated to permit movement, and then pushed distally of the predilated stenosis. Next, the physician slides a balloon catheter over the balloon-on-a-wire assembly and to the stenosis, without passing over the balloon of the balloon-on-a-wire assembly. Subsequent inflation and deflation further dilate the stenosis, usually completing the procedure. If needed, the physician may exchange the balloon catheter for a larger one in order to further dilate the stenosis. The physician again leaves the balloon-on-a-wire assembly in place to guide the larger balloon catheter to and through the stenosis.

The present invention recognizes that it is unnecessary to design a balloon-on-a-wire assembly to pass through the balloon catheter. This recognition permits the present invention to feature advances which benefit the physician and the patient. Previous approaches have required removal of a previously inserted guidewire, microdilation probe, dilating guidewire, or similar device, in some instances through the balloon catheter, in order to complete a multiple dilation procedure. Such poses additional risk to the patient and uses the physician's time inefficiently by requiring multiple insertions and/or removals of components. The present invention saves physician time, reduces risk to the patient, and allows more patients to realize the advantages of angioplasty procedures.

Previous approaches such as those of U.S. Pat. No. 5,102,390, even if initial insertion of a dilating microprobe is practiced, still require the passage of the entire body of the probe, including its deflated balloon, through the lumen of the balloon catheter. By the present invention, the balloon of the microdilation probe, or balloon-on-a-wire assembly, does not pass through the balloon catheter, but the balloon catheter passes over the elongated body of the wire assembly which may include a proximal extension thereof. The balloon-on-a- wire assembly truly functions as a delivery system for the balloon catheter.

Since the balloon of the balloon-on-a-wire assembly of the present invention does not pass through the lumen of the balloon catheter, the inner chamber of the balloon catheter may be made smaller. Likewise the outer diameter of the balloon catheter can also be smaller, permitting insertion into tighter stenoses. Because the balloon catheter can be inserted into tighter stenoses, the balloon-on-a-wire assembly may not need to predilate the stenosis as widely. Because the predilation requirements are smaller when compared with other approaches, the uninflated balloon profile may be made relatively smaller than heretofore possible. Patients who require heart bypass surgery because their stenoses are too tight may now be able to use an angioplasty procedure.

BRIEF DESCRIPTION OF THE DRAWINGS

In the course of this description, reference will be made to the attached drawings, wherein:

FIG. 1 is a broken-away elevational view of the balloon-on-a-wire assembly inserted, prior to inflation, into a vessel shown in cross-section;

FIG. 2 shows the balloon-on-a-wire assembly inflated to perform an initial dilation, or to predilate, a stenosis of the vessel;

FIG. 3 shows the balloon-on-a-wire assembly moved distally of the predilated stenosis;

FIG. 4 illustrates the hub of the balloon on a wire assembly being physically removed from the assembly;

FIG. 5 illustrates the use of an extension wire affixed to the proximal end of the balloon-on-a-wire assembly;

FIG. 6 is a broken-away elevational view showing a balloon catheter slidingly inserted over the balloon-on-a-wire assembly;

FIG. 7 is a view similar to FIG. 6 which illustrates inflation of the balloon of the balloon catheter to further dilate the stenosis;

FIG. 8 shows removal of the deflated balloon catheter while leaving the balloon-on-a-wire in place; and FIG. 9 depicts removal of the balloon-on-a-wire assembly from the vessel.

DESCRIPTION OF THE PREFERRED EMBODIMENTS

FIGS. 1 through 9 demonstrate a preferred procedure and illustrate a preferred embodiment of the combination catheter system according to the present invention. FIG. 1 shows a fixed wire percutaneous transluminal angioplasty balloon dilatation catheter, or balloon-on-a-wire assembly, generally designated as 21, inserted into a body vessel 22, such as a blood vessel, having a stenosis 23.

A hub 24 is positioned on the proximal end of the balloon-on-a-wire assembly 21. Hub 24, in accordance with generally known principles, facilitates connection of assembly 21 to equipment for carrying out desired medical procedures. For example, the hub 24 cooperates in providing steering control, enabling the physician to maneuver the distal end of the assembly 21 through arterial branches and to the stenosis. The hub 24 also serves as a manifold to communicate pressurized fluid to and through the assembly 21.

Balloon-on-a-wire assembly 21 further includes an elongated body or wire 25 having a balloon member 26. Typically, the wire 25 has an outer shaft diameter of about 0.018" or less, giving it size and performance characteristics comparable those of a standard guidewire used for inserting angioplasty catheters. Wire 25 may be an assembly of a solid core and a cylindrical tube with an annular space between these two members. Alternatively, the wire may be a hollow core wire having an axial space. In either event, pressurized fluid flows from the hub 24 to the balloon member 26 within the wire 25, through either the annular space or the axial space. The wire 25 is sufficiently flexible to permit maneuvering through arterial branches and stenoses, while being sufficiently stiff to prevent folding and buckling of it and of catheters inserted over it.

With reference to the distal portion of the assembly 21, it is designed to exhibit material thickness, strength, elasticity, inflation diameter, and uninflated profile properties that are optimal for these types of devices, which properties are generally appreciated by those skilled in the art. The balloon is inserted, typically through the arterial system or other body vessel and to the stenosis, in an uninflated state as illustrated in FIG. 1. Tip portion 27 of wire 25 typically is simply the end of the wire with no additional parts being required, although a distal coil could be utilized. It may be tapered to improve maneuverability or blunted to minimize the chance of arterial trauma. The wire 25 is closed distally to prevent leakage of the pressurized fluid into the bloodstream or the like and to permit the requisite degree of pressurization within the wire to suitably inflate the balloon 26. Such distal closure will be provided, for example, at the distal seal area of the balloon to the assembly 21 or nearer to the end 28 of the tip portion 27, the precise location typically depending upon the specific structure of the wire 25.

FIG. 2 shows inflation of the balloon 26 within the stenosis 23. The balloon is inflated with pressurized fluid passing through the hub 24 and communicated along or through the wire 25. The pressurized fluid is usually an inert solution, such as a saline solution. Once the stenosis has been initially dilated or predilated with the assembly 21—that is dilated sufficiently to permit insertion of the balloon catheter—the physician deflates the balloon 26, such as by drawing the fluid out through the hub in accordance with generally known procedures to remove same from the predilated stenosis 23a. FIG. 3 shows distally directed movement of the deflated balloon-on-a-wire assembly 21 to a location distal of the predilated stenosis. Note that the deflated balloon itself is distal of the predilated stenosis.

FIG. 4 generally illustrates separation of the hub 24 from the wire 25. The hub may be removed by any of several means, including pulling, breaking, snapping, unscrewing or cutting from the wire in order to provide a balloon-on-a-wire assembly 21 that is free of obstructions which would prevent unhindered passage of the balloon catheter thereover. In some instances, the wire 25 may be of an adequate length to fully accommodate the balloon catheter. It may be necessary to extend the length of the wire once the hub has been removed. FIG. 5 shows the addition of an extension 29 to the wire 25. The extension 29 may be affixed to wire 25 by any suitable means, such as with a cinch-type device or other concentric sleeve 31 as illustrated or by the use of a rod positioned within both the wire and the extension. Any sleeve 31 should have an external profile sized and shaped to permit substantially unobstructed passage of a balloon catheter thereover.

FIG. 6 depicts insertion of a balloon catheter assembly, generally designated as 32, into the body vessel 22 and to the location of the predilated stenosis 23a. The wire 25 and (when provided) extension 29 are used as a delivery system to accurately and quickly deliver the balloon catheter assembly 32 to the stenosis. Balloon 33 of the balloon catheter assembly 32 is shown inserted into the predilated stenosis, while body 34 thereof is slidably mounted over body 25 of the balloon-on-a-wire assembly 21. A hub 35 of the balloon catheter assembly 32 is provided for reasons appreciated by those in the art, for example performing as a manifold to communicate pressurized fluid through the catheter body 34 to the balloon 33. Junction 36 permits insertion of the balloon catheter assembly 32 over the balloon-on-a-wire assembly 21 while preserving isolated fluid communication from hub 35 to balloon 33.

FIG. 7 illustrates inflation of the balloon 33 to further dilate the lesion or stenosis when pressurized fluid, usually an inert solution such as a saline solution, is passed into the balloon catheter assembly 32 by way of the hub 35. A dilated stenosis 23b is shown. FIG. 8 illustrates the balloon 33 deflated and the balloon catheter 32 in the process of being removed along the balloon-on-a-wire assembly 21. In an important aspect of this invention, the balloon-on-a-wire assembly 21 remains in place during this procedure. In fact, once the balloon-on-a-wire assembly 21 is moved slightly distally as shown in FIG. 3, it remains substantially in place through the angioplasty procedure, with its deflated balloon 26 positioned just distally of the lesion or stenosis.

Finally, FIG. 9 shows removal of the balloon-on-a-wire assembly 21 from the blood vessel 22 or the like, with the angioplasty procedure having been completed. No additional removal step, such as removal of a guidewire, is required, and the balloon-on-a-wire delivery system for the balloon catheter is inserted and removed only once during the entire procedure.

It will be understood that the embodiments of the present invention which have been described are illustrative of some of the applications of the principles of the present invention. Numerous modifications may be made by those skilled in the art without departing from the true spirit and scope of the invention.

We claim:

1. A multiple component balloon catheter system, comprising:
    a fixed wire percutaneous transluminal angioplasty balloon dilatation catheter which is a balloon-on-a-wire assembly having a elongated body with a balloon member at a distal portion thereof, said elongated body being a wire-like member having a lumen, said lumen communicating pressurized fluid between a proximal end portion of the balloon-on-a-wire assembly and said balloon member, said elongated body having an outer diameter substantially the same as that of a catheter guidewire; and
    an over-the-wire percutaneous transluminal angioplasty balloon catheter, said over-the-wire balloon catheter having an elongated body with a balloon member at a distal end portion thereof, said elongated body being a tubular member having a lumen for communicating pressurized fluid between a proximal end portion of the over-the-wire catheter and its said balloon member, said lumen exhibiting an inner diameter which is slightly larger than said outer diameter of the elongated body of the balloon-on-a-wire assembly and which is smaller than the external sizing of the said balloon of the balloon-on-a-wire assembly when said balloon is deflated, said over-the-wire balloon catheter is slidably insertable over the elongated body of the balloon-on-a-wire assembly but not slidable over said balloon member of the balloon-on-a-wire assembly.

2. The multiple component balloon catheter system in accordance with claim 1, wherein said balloon-on-a-wire assembly includes an elongated extension member secured to a proximal end of said elongated body of the balloon-on-a-wire assembly, said elongated extension member having an outer diameter not greater than that of said outer diameter of the elongated body of the balloon-on-a-wire assembly.

3. The multiple component balloon catheter system in accordance with claim 1, wherein said balloon-on-a-wire assembly includes a hub member at a proximal end of said elongated body thereof, said hub member being removable after insertion of the balloon-on-a-wire assembly within a living body vessel, said balloon-on-a-wire assembly further including an elongated extension member which is secured to the proximal end after removal of said hub member, said elongated extension member having an outer diameter not greater than said outer diameter of the elongated body of the balloon-on-a-wire assembly.

4. The multiple component balloon catheter system in accordance with claim 3, wherein said elongated extension member is secured to said proximal end by a sleeve member.

5. An angioplasty procedure for treating a stenosis within a living body vessel, comprising the steps of:
    inserting into a body vessel a fixed wire percutaneous transluminal angioplasty balloon dilation catheter which is a balloon-on-a-wire assembly having an elongated body with a balloon member at a distal end portion thereof;
    locating the balloon member within a stenosis of the body vessel, inflating the balloon member to predilate the stenosis, and deflating the balloon member to provide a deflated balloon member;
    moving the balloon-on-a-wire assembly distally within the body vessel to a location such that the balloon member is closely distally spaced from the predilated stenosis;
    providing an over-the-wire percutaneous transluminal angioplasty balloon catheter having a lumen substantially along its entire length, which lumen is sized to prevent the deflated balloon member from passing into the lumen;
    slidably inserting the over-the-wire percutaneous transluminal angioplasty balloon catheter into the body vessel while passing its lumen over the elongated body of the balloon-on-a-wire assembly until the angioplasty balloon thereof is located at the stenosis which had been predilated and without passing the over-the-wire catheter over the deflated balloon member of the balloon-on-a-wire assembly;
    dilating the stenosis by inflating the angioplasty balloon of the over-the-wire catheter, and deflating the angioplasty balloon; and
    removing the over-the-wire catheter and the balloon-on-a-wire assembly from the body vessel.

6. An angioplasty procedure for treating a stenosis within a living body vessel, comprising the steps of:
    inserting into a body vessel a fixed wire percutaneous transluminal angioplasty balloon dilation catheter which is a balloon-on-a-wire assembly having an elongated body with a balloon member at a distal end portion thereof;

locating the balloon member within a stenosis of the body vessel, inflating the balloon member to predilate the stenosis, and deflating the balloon member;

moving the balloon-on-a-wire assembly distally within the body vessel to a location such that the balloon member is closely distally spaced from the predilated stenosis;

securing an extension member to a proximal end of the elongated body of the balloon-on-a-wire assembly;

slidably inserting an over-the-wire percutaneous transluminal angioplasty balloon catheter into the body vessel and over the elongated body of the balloon-on-a-wire assembly until the angioplasty balloon thereof is located at the stenosis which had been predilated and without passing the over-the-wire catheter over the balloon member of the balloon-on-a-wire assembly and said slidably inserting step further includes passing the over-the-wire catheter over the extension member;

dilating the stenosis by inflating the angioplasty balloon of the over-the-wire catheter, and deflating the angioplasty balloon; and removing the over-the-wire catheter and the balloon-on-a-wire assembly from the body vessel.

7. An angioplasty procedure for treating a stenosis within a living body vessel, comprising the steps of:

inserting into a body vessel a fixed wire percutaneous transluminal angioplasty balloon dilation catheter which is a balloon-on-a-wire assembly having an elongated body with a balloon member at a distal end portion thereof, the balloon-on-a-wire assembly having a hub at its proximal end portion;

locating the balloon member within a stenosis of the body vessel, inflating the balloon member to predilate the stenosis, and deflating the balloon member;

moving the balloon-on-a-wire assembly distally within the body vessel to a location such that the balloon member is closely distally spaced from the predilated stenosis;

removing the hub from the proximal end portion of the balloon-on-a-wire assembly;

slidably inserting an over-the-wire percutaneous transluminal angioplasty balloon catheter into the body vessel and over the elongated body of the balloon-on-a-wire assembly until the angioplasty balloon thereof is located at the stenosis which had been predilated and without passing the over-the-wire catheter over the balloon member of the balloon-on-a-wire assembly;

dilating the stenosis by inflating the angioplasty balloon of the over-the-wire catheter, and deflating the angioplasty balloon; and removing the over-the-wire catheter and the balloon-on-a-wire assembly from the body vessel.

8. The angioplasty procedure in accordance with claim 7, wherein the step of removing the hub from the proximal end portion of the balloon-on-a-wire assembly is followed by a step of securing an extension member to the proximal end portion from which the hub had been removed during said removing step.

9. An angioplasty procedure for treating a stenosis within a living body vessel, comprising the steps of:

inserting into a body vessel a fixed wire percutaneous transluminal angioplasty balloon dilation catheter which is a balloon-on-a-wire assembly having an elongated body with a balloon member at a distal end portion thereof;

locating the balloon member within a stenosis of the body vessel, inflating the balloon member to predilate the stenosis, and deflating the balloon member to provide a deflated balloon member;

moving the balloon-on-a-wire assembly distally within the body vessel to a location such that the balloon member is closely distally spaced from the predilated stenosis;

slidably inserting an over-the-wire percutaneous transluminal angioplasty balloon catheter into the body vessel and over the elongated body of the balloon-on-a-wire assembly until the angioplasty balloon thereof is located at the stenosis which had been predilated and without passing the over-the-wire catheter over the balloon member of the balloon-on-a-wire assembly;

said slidably inserting step includes preventing passage of the over-the-wire catheter over the deflated balloon member of the balloon-on-a-wire assembly by relative sizing of a lumen of the over-the-wire catheter and of the deflated balloon member of the balloon-on-a-wire assembly whereby the deflated balloon member will not pass through the lumen;

dilating the stenosis by inflating the angioplasty balloon of the over-the-wire catheter, and deflating the angioplasty balloon; and removing the over-the-wire catheter and the balloon-on-a-wire assembly from the body vessel.

10. An angioplasty procedure for treating a stenosis within a living body vessel, comprising the steps of:

inserting into a body vessel a fixed wire percutaneous transluminal angioplasty balloon dilation catheter which is a balloon-on-a-wire assembly having an elongated body with a balloon member at a distal end portion thereof;

locating the balloon member within a stenosis of the body vessel, inflating the balloon member to predilate the stenosis, and deflating the balloon member;

moving the balloon-on-a-wire assembly distally within the body vessel to a location such that the balloon member is closely distally spaced from the predilated stenosis;

slidably inserting an over-the-wire percutaneous transluminal angioplasty balloon catheter into the body vessel and over the elongated body of the balloon-on-a-wire assembly until the angioplasty balloon thereof is located at the stenosis which had been predilated and without passing the over-the-wire catheter over the balloon member of the balloon-on-a-wire assembly;

dilating the stenosis by inflating the angioplasty balloon of the over-the-wire catheter, and deflating the angioplasty balloon; and removing the over-the-wire catheter and the balloon-on-a-wire assembly from the body vessel, the over-the-wire catheter being removed prior to removal of the balloon-on-a-wire assembly.

* * * * *